United States Patent [19]
Roark et al.

[11] Patent Number: 5,807,846
[45] Date of Patent: Sep. 15, 1998

[54] PHOSPHONAMIDE ACAT INHIBITORS

[75] Inventors: William Howard Roark, Ann Arbor; Bruce David Roth, Plymouth, both of Mich.

[73] Assignee: Warner-Lambert Company, Morris Plains, N.J.

[21] Appl. No.: 881,483

[22] Filed: Jun. 24, 1997

Related U.S. Application Data

[60] Provisional application No. 60/031,234 Nov. 14, 1996.
[51] Int. Cl.$^6$ .................................................. A61K 31/66
[52] U.S. Cl. .......................... 514/120; 514/110; 514/114; 558/195; 558/199; 558/178
[58] Field of Search ...................... 514/110, 114, 514/120, 76; 558/195, 199, 178; 504/199

[56] References Cited

U.S. PATENT DOCUMENTS

| 4,627,870 | 12/1986 | Nagubandi | 546/24 |
| 4,849,488 | 7/1989 | Starzewski et al. | 526/193 |
| 5,013,854 | 5/1991 | Bunnell | 549/496 |
| 5,084,568 | 1/1992 | Bunnell | 540/487 |
| 5,208,224 | 5/1993 | Bolton | 514/110 |
| 5,412,097 | 5/1995 | Chakravarty et al. | 546/118 |
| 5,494,983 | 2/1996 | Reetz | 526/194 |

FOREIGN PATENT DOCUMENTS

| 258601 | 7/1988 | Germany . |
| 63-312349 | 12/1988 | Japan . |
| 9008151 | 7/1990 | WIPO . |

OTHER PUBLICATIONS

J Chem Soc Perkins Trans 1, Eli Breuer, (12) pp. 3263–3269, Dec. 1990.
Beilstein, Brn=285976, Abst of J Gen Chem USSR, Derkatsch, 35, p. 1019, 1965.
CA:90:87579, abst of "Alkyl esters of acylamidophosphoric and acylamidoalkyl(aryl)phosphonic acids", Zagnibeda, Khim Yekhnol 101 pp. 21–24, 1978.

*Primary Examiner*—Gary Geist
*Assistant Examiner*—Jean F. Vollano
*Attorney, Agent, or Firm*—Elizabeth M. Anderson

[57] ABSTRACT

The present invention is directed to compounds useful for the regulation of cholesterol of Formula I, methods for using them and pharmaceutical compositions thereof, $$Ar-X-\underset{\underset{OR}{|}}{\overset{\overset{O}{\|}}{P}}-\underset{H}{\overset{}{N}}-\overset{\overset{O}{\|}}{C}-(CH_2)_{0-4}-Ar^1 \qquad I$$

wherein

Ar and $Ar^1$ are each independently selected from unsubstituted or substituted phenyl which substituents are from 1–5 in number and are each independently selected from alkyl, alkoxy, hydroxy, halogen, nitro, trifluoromethyl, COOH, and COOalkyl;

X is —NH—, —O—, —S—, or —$(CH_2)_{0-4}$—, and

R is hydrogen, alkyl, or phenyl.

7 Claims, No Drawings

1

PHOSPHONAMIDE ACAT INHIBITORS

This application claims the benefit of U.S. provisional application No. 60/031,234 filed Nov. 14, 1996.

BACKGROUND OF INVENTION

This invention relates to chemical compounds having pharmacological activity, to pharmaceutical compositions which include these compounds, and to pharmaceutical methods of treatment. More particularly, this invention concerns certain phosphonamides which inhibit the enzyme, acyl-coenzyme A:cholesterol acyltransferase (ACAT), pharmaceutical compositions containing these compounds, and methods of treating hypercholesterolemia and atherosclerosis.

In recent years the role which elevated blood plasma levels of cholesterol plays in pathological conditions in man has received much attention. Deposits of cholesterol in the vascular system have been indicated as causative of a variety of pathological conditions including coronary heart disease.

Initially, studies of this problem were directed toward finding therapeutic agents which would be effective in lowering total serum cholesterol levels. It is now known that cholesterol is transported in the blood in the form of complex particles consisting of a core of cholesteryl esters plus triglycerides and a variety of types of protein which are recognized by specific receptors. For example, cholesterol is carried to the sites of deposit in blood vessels in the form of low density lipoprotein cholesterol (LDL cholesterol) and away from such sites of deposit by high density lipoprotein cholesterol (HDL cholesterol).

Following these discoveries, the search for therapeutic agents which control serum cholesterol turned to finding compounds which are more selective in their action; that is, agents which are effective in elevating the blood serum levels of HDL cholesterol and/or lowering the levels of LDL cholesterol. While such agents are effective in moderating the levels of serum cholesterol, they have little or no effect on controlling the initial absorption of dietary cholesterol in the body through the intestinal wall.

In intestinal mucosal cells, dietary cholesterol is absorbed as free cholesterol which must be esterified by the action of the enzyme, acyl-CoA:cholesterol acyltransferase (ACAT) before it can be packaged into the chylomicrons which are then released into the blood stream. Thus, therapeutic agents which effectively inhibit the action of ACAT prevent the intestinal absorption of dietary cholesterol into the blood stream or the reabsorption of cholesterol which has been previously released into the intestine through the body's own regulatory action.

SUMMARY OF THE INVENTION

The present invention is directed to compounds of Formula I below, methods for using the compounds of Formula I, pharmaceutical compositions thereof, and processes for preparing the compounds.

The invention is compounds of formula $$\text{Ar}-X-\underset{\underset{OR}{|}}{\overset{\overset{O}{\|}}{P}}-\underset{\underset{H}{|}}{N}-\overset{\overset{O}{\|}}{C}-(CH_2)_{\overline{0-4}}-Ar^1 \quad I$$

or a pharmaceutically acceptable salt thereof wherein:

Ar and $Ar^1$ are each independently selected from unsubstituted or substituted phenyl which substituents are from 1–5 in number and are each independently selected from alkyl, alkoxy, hydroxy, halogen, nitro, trifluoromethyl, COOH, and COOalkyl;

X is —NH—, —O—, —S—, or —$(CH_2)_{0-4}$—; and

R is hydrogen, alkyl, phenyl, or sodium.

Preferred compounds of the invention are those of Formula I wherein

Ar is phenyl;

$Ar^1$ is phenyl;

X is —NH—, —O—, —S—, or —$(CH_2)_{0-4}$—; and

R is hydrogen, alkyl, phenyl, or sodium.

More preferred compounds are those of Formula I wherein

Ar is phenyl substituted with 3 substituents each independently selected from isopropyl, hydrogen, and chloride;

$Ar^1$ is phenyl substituted with 3 substituents each independently selected from isopropyl and hydrogen; and X is $CH_2$ or O.

Most preferred compounds are, for example,

Phosphonamidic acid, N-[[2,6-bis(1-methyl-ethyl) phenyl) acetyl]-P-[[2,4,6-tris(1-methyl-ethyl)phenyl) methyl]-, methyl ester;

[(2,4,6-Triisopropyl-phenyl)-acetyl]-phosphor-amidic acid 2,6-diisopropyl-phenyl ester methyl ester;

Phosphoramidic acid, [[[2,6-bis(1-methylethyl)phenyl] amino]carbonyl]-, methyl 2,6-bis(1-methylethyl) phenyl ester;

[(2,4,6-Triisopropyl-phenyl)-acetyl]-phosphonamidic acid 4-chloro-2,6-diisopropyl-phenyl ester methyl ester;

Phosphonamidic acid, P-phenyl-N-[[2,4,6-tris(1-methylethyl)phenyl]acetyl]-, 2,6-bis(1-methylethyl) phenyl ester Phosphonamidic acid, P-[[2,6-bis(1-methylethyl)phenyl] methyl]-N-[[2,4,6-tris(1-methylethyl)phenyl]acetyl]-, methyl ester; and Phosphonamidic acid, N-[[2,4,6-tris(1-methylethyl) phenyl]acetyl]-P-[[2,4,6-tris(1-methylethyl)phenyl] methyl]-, methyl ester.

The invention is also a pharmaceutical composition for regulating plasma cholesterol concentrations comprising a therapeutically effective amount of a compound of Formula I above and a pharmaceutically acceptable carrier.

The invention is also a method of treating hypercholesterolemia and/or atherosclerosis comprising administering to a patient a therapeutically effective amount of a compound of Formula I above in unit dosage form.

DETAILED DESCRIPTION

In Formula I above, illustrative examples of straight or branched saturated alkyl chains having from 1 to 20 carbon atoms include methyl, ethyl, n-propyl, isopropyl, n-butyl, iso-butyl, tert-butyl, n-pentyl, isopentyl, n-hexyl, n-heptyl, n-octyl, n-undecyl, n-dodecyl, n-hexadecyl, 2,2-dimethyldodecyl, 2-tetradecyl, and n-octadecyl groups.

Illustrative examples of straight or branched alkyl chains having from 1 to 20 carbon atoms and having from 1 to 3 double bonds include ethenyl, 2-propenyl, 2-butenyl, 3-pentenyl, 2-octenyl, 5-nonenyl, 4-undecenyl, 5-heptadecenyl, 3-octadecenyl, 9-octadecenyl, 2,2-dimethyl-11-eicosenyl, 9,12-octadecadienyl, and hexadecenyl.

Straight or branched alkoxy groups having from 1 to 6 carbon atoms include, for example, methoxy, ethoxy, n-propoxy, t-butoxy, and pentyloxy.

Illustrative examples of straight or branched alkyl groups having from 1 to 6 carbon atoms as used in Formula I include methyl, ethyl, n-propyl, isopropyl, n-pentyl, n-butyl, and tert-butyl.

Pharmaceutically acceptable salts of the compounds of Formula I are also included as a part of the present invention.

The base salts may be generated from compounds of Formula I by reaction of the latter with one equivalent of a suitable nontoxic, pharmaceutically acceptable base followed by evaporation of the solvent employed for the reaction and recrystallization of the salt, if required. The compounds of Formula I may be recovered from the base salt by reaction of the salt with an aqueous solution of a suitable acid such as hydrobromic, hydrochloric, or acetic acid.

Suitable bases for forming base salts of the compounds of this invention include amines such as triethylamine or dibutylamine, or alkali metal bases and alkaline earth metal bases. Preferred alkali metal hydroxides and alkaline earth metal hydroxides as salt formers are the hydroxides of lithium, sodium, potassium, magnesium, or calcium. The class of bases suitable for the formation of nontoxic, pharmaceutically acceptable salts is well known to practitioners of the pharmaceutical formulation arts. See, for example, Berge S N, et al, *J Pharm Sci* 1977; 66: 1–19.

Suitable acids for forming acid salts of the compounds of this invention containing a basic group include, but are not necessarily limited to acetic, benzoic, benzenesulfonic, tartaric, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. The acid addition salts are formed by procedures well known in the art.

The compounds of the present invention may also exist in different stereoisomeric forms by virtue of the presence of asymmetric centers in the compound. The present invention contemplates all stereoisomeric forms of the compounds as well as mixtures thereof, including racemic mixtures.

Further, the compounds of this invention may exist in unsolvated as well as solvated forms with pharmaceutically acceptable solvents such as water, ethanol and the like. In general, the solvated forms are considered equivalent to the unsolvated forms for the purposes of this invention.

As shown by the data presented below in Table 1, the compounds of the present invention are inhibitors of the enzyme acyl-CoA:cholesterol acyltransferase (ACAT), and are thus effective in inhibiting the esterification and transport of cholesterol across the intestinal cell wall. The compounds of the present invention are thus useful in pharmaceutical formulations for the treatment of hypercholesterolemia or atherosclerosis.

The ability of representative compounds of the present invention to inhibit ACAT was measured using an in vitro test more fully described in Field F J, Salone R G, *Biochemica et Biophysica*, 1982; 712: 557–570. The test assesses the ability of a test compound to inhibit the acylation of cholesterol by oleic acid by measuring the amount of radiolabeled cholesterol oleate formed from radiolabeled oleic acid in a tissue preparation containing rat liver microsomes.

The data appear in Table 1 where they are expressed in $IC_{50}$ values; i.e., the concentration of test compound required to inhibit the activity of the enzyme by 50%.

In one in vivo screen designated APCC, male Sprague-Dawley rats (200 to 225 g) were randomly divided into treatment groups and dosed at 4 PM with either vehicle (CMC/Tween) or suspensions of compounds in vehicle. The normal chow diet was then replaced with a high fat, high cholesterol diet (designated PCC) containing 0.5% cholic acid. The rats consumed this diet ad libitum during the night and were sacrificed at 8 AM to obtain blood samples for cholesterol analysis using standard procedures. Statistical differences between mean cholesterol values for the same vehicle were determined using analysis of variance followed by Fisher's least significant test. The results of this trial for representative compounds of the present invention appear in Table 1.

TABLE 1

Phosphonamide ACAT Inhibitors

| A | B | R | X | $LAI(10^{-6}M)$ | APCC (dose mg/kg) |
|---|---|---|---|---|---|
| iPr | H | $OCH_3$ | $CH_2$ | 0.29 | −44 (3) |
| iPr | H | $OCH_3$ | O | 4.8 | −18 (1) |
| H | H | $OCH_3$ | O | 0.95 | −33 (10) |
| Cl | iPr | $OCH_3$ | O | >5 | −12 (10) |
| H | iPr | Ph | O | 2.5 | −25 (10) |
| H | iPr | $OCH_3$ | $CH_2$ | 1.2 | |
| iPr | iPr | $OCH_3$ | $CH_2$ | 0.74 | |
| Monobenzyl,2,4,6-triisopropylbenzyl-phosphonamide | | | | 3.6 | −4 (10) |
| Monobenzyl,2,4,6-triisopropylbenzyl-phosphonic chloride | | | | 51.5 | −28 (10) | not tested not tested

In therapeutic use as agents for treating hypercholesterolemia or atherosclerosis, the compounds of Formula I or pharmaceutically acceptable salts thereof are administered to the patient at dosage levels of from 250 to 3000 mg per day. For a normal human adult of approximately 70 kg of body weight, this translates into a dosage of from 5 to 40 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing the pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

Powders and tablets preferably contain between about 5% to about 70% by weight of the active ingredient. Suitable carriers are magnesium dicarbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner cachets or transdermal systems are also included.

Tablets, powders, cachets, and capsules can be used as solid dosage forms suitable for oral administration.

Liquid form preparations include solutions, suspensions, or emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethylcellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation containing discrete quantities of the preparation, for example, packeted tablets, capsules, and powders in vials or ampoules. The unit dosage form can also be a capsule, cachet, or tablet itself, or it can be the appropriate number of these packaged forms.

SCHEME I

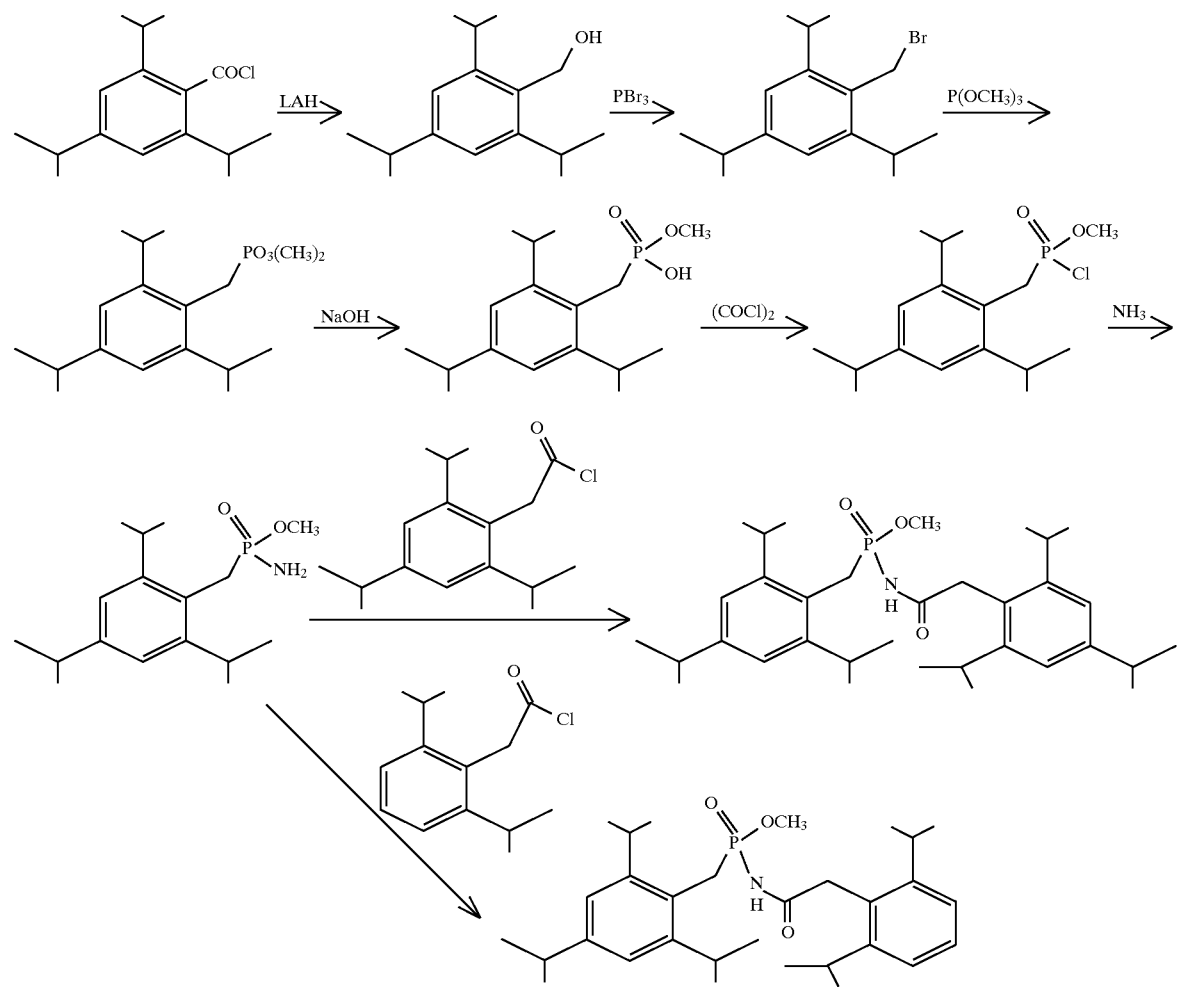

-continued
SCHEME I
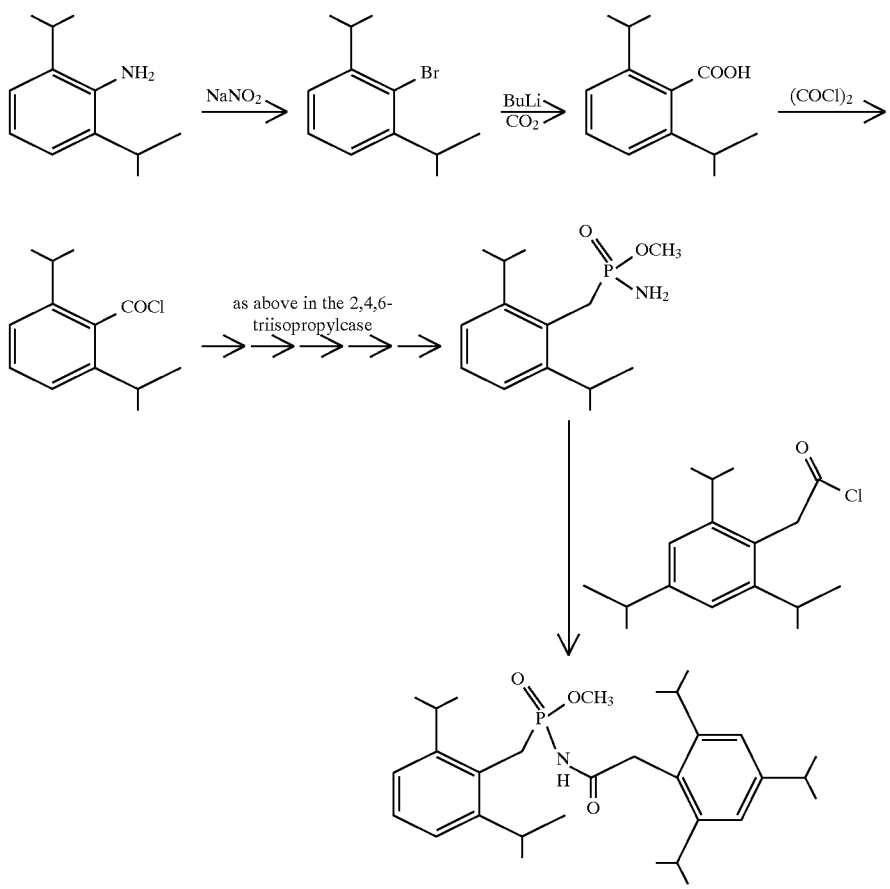
SCHEME II
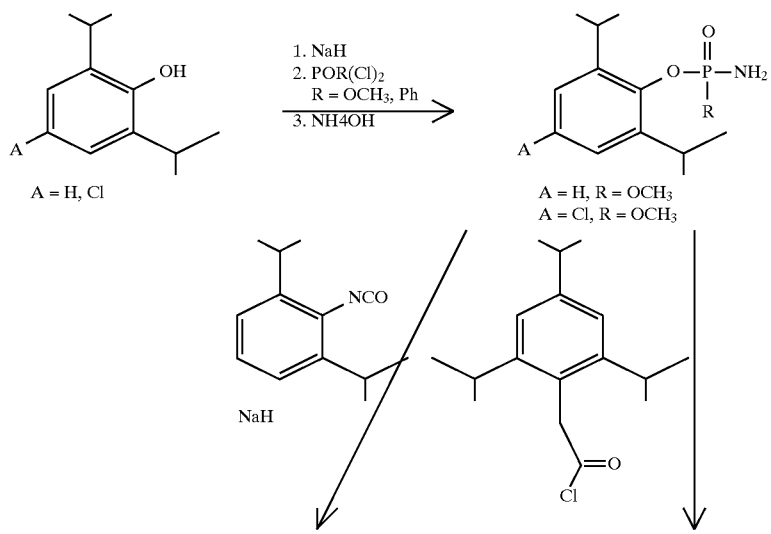

-continued
SCHEME II

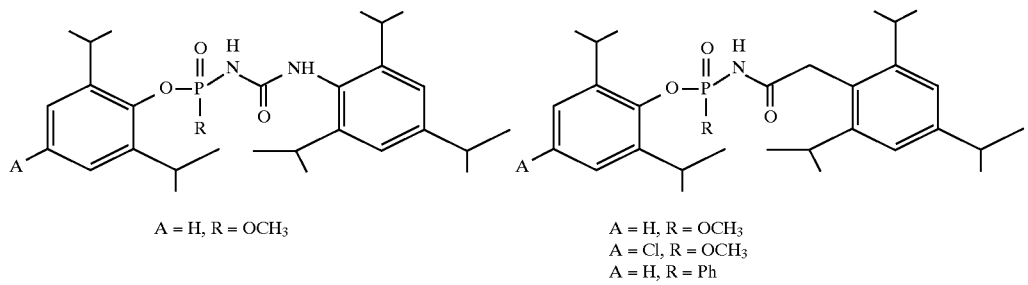

A = H, R = OCH₃

A = H, R = OCH₃
A = Cl, R = OCH₃
A = H, R = Ph

EXAMPLES

The following examples illustrate techniques discovered by the inventors for the preparation of the compounds of the present invention. It should be appreciated by those of skill in the art that the techniques disclosed in the examples which follow represent laboratory techniques discovered by the inventors to function well in the practice of the invention, and thus can be considered to constitute preferred modes for this practice. Those of skill in the art should, however, in light of the present disclosure, appreciate that many changes can be made in the specific embodiments which are disclosed and still obtain a like or similar result without departing from the spirit and scope of the invention. In other words, the following examples are given to illustrate particular compositions and methods within the scope of the present invention and are not intended to limit the scope of the present invention.

2,4,6-Triisopropylbenzyl alcohol

A solution of 2,4,6-triisopropylbenzoyl chloride (24.96 g, 0.094 mol) in ethyl ether (150 mL) was added in portions over 1 hour to lithium aluminum hydride (3.70 g, 0.097 mol) in ethyl ether (300 mL) keeping the temperature between −15° C. and −30° C. The reaction mixture was allowed to warm to room temperature over about 1 hour. The reaction mixture was cooled to 0° C. and quenched by adding saturated aqueous sodium bisulfate solution. The layers were separated, the aqueous layer was back-extracted with ethyl acetate, the organic layers were combined and dried (magnesium sulfate), filtered, and concentrated to a white solid (21.50 g, 98% crude). An analytical sample was obtained by filtering 1.0 g through silica gel using hexanes, then 5% ethyl acetate in hexanes as eluant yielding 0.778 g of the product as a white solid.

2,4,6-Triisopropylbenzyl bromide

A solution of phosphorus tribromide (3.8 mL, 0.04 mol) in ethyl ether (150 mL) was added dropwise to 2,4,6-triisopropylbenzyl alcohol (17.99 g, 0.076 mol) in ethyl ether (350 mL) at room temperature under a nitrogen atmosphere. The reaction mixture was stirred overnight at room temperature. Ethanol (95%, 50 mL) was added dropwise over 1 hour and the resulting mixture was stirred for 30 minutes, and was then concentrated to an oil. The oil was partitioned between ethyl acetate (300 mL) and saturated aqueous sodium bicarbonate. The organic layer was washed with water (50 mL), dried (magnesium sulfate), filtered, and concentrated to a clear liquid (22.56 g, 98.9%). This was used directly in the next step.

Dimethyl,2,4,6-triisopropylbenzyl phosphonate

A mixture of 2,4,6-triisopropylbenzyl bromide (22.3 g, 0.075 mol) and trimethyl phosphite (100 mL, 0.81 mol) was gradually warmed to 124° C. over 3.5 hours. The reaction mixture was stirred overnight at room temperature and was then gradually warmed to 148° C. at which time the temperature cooled to 105° C. The reaction mixture was heated 4 additional hours and was then allowed to cool to room temperature. The reaction mixture was poured into water (800 mL) and stirred vigorously at room temperature for 2 hours. The aqueous solution was extracted with ethyl acetate (1×500 mL and 1×150 mL), the combined extracts washed several times with water, dried (magnesium sulfate), filtered and concentrated to an oil which crystallized yielding the product as a white solid (24.10 g, 98.4%). An analytical sample was prepared by filtration of 0.5 g of the product through silica gel giving 0.367 g of product. Analysis calculated for ($C_{18}H_{31}O_3P$).

Monomethyl, 2,4,6-triisopropylbenzyl phosphonate

A mixture of dimethyl, 2,4,6-triisopropylbenzyl phosphonate (23.6 g, 0.072 mol), sodium hydroxide (5.78 g, 0.145 mol), methanol (150 mL, and water (100 mL) was heated on the steambath for 5 hours and was then allowed to stand overnight at room temperature. The reaction mixture was then heated for 8 hours on the steambath adding methanol as needed to get solution. The reaction mixture was allowed to stand overnight at room temperature and was then concentrated at 70° C. to remove methanol, diluted with water, washed with ethyl acetate, made acidic with citric acid (10% aqueous), extracted into ethyl acetate, dried (magnesium sulfate), filtered, and concentrated to an oil which crystallized. Hexanes was added to the solid and the solid collected by filtration. Two crops were obtained, 15.76 g, 69.7%. Analysis calculated for ($C_{17}H_{29}O_3P$).

Monomethyl, 2,4,6-triisopropylbenzylphosphonic chloride

A mixture of monomethyl, 2,4,6-triisopropylbenzyl phosphonate (4.91 g, 0.016 mol), oxalyl chloride (19 mL), and dimethylformamide (2 drops) was stirred overnight at room temperature and then concentrated to a light yellow solid, 5.3 g, 100%.

Monomethyl, 2,4,6-triisopropylbenzylphosphonamide

Monomethyl, 2,4,6-triisopropylbenzylphosphonic chloride (1.5 g, 0.0045 mol) in ethyl ether (50 mL) was added to a rapidly stirred mixture of ethyl ether (100 mL) and concentrated aqueous ammonia. The reaction mixture was stirred 3 hours at room temperature, the layers separated, the organic layer washed with brine, dried (magnesium sulfate), filtered, and concentrated to a white solid, 1.27 g, 90%. Analysis calculated for ($C_{17}H_{30}NO_2P$).

2,6-Diisoproylphenyltriflate

Triflic anhydride (50.0 g) was added dropwise to a mixture of 2,6-diisopropylphenol (33 mL) in pyridine (300 mL) keeping the temperature below −20° C. Upon completing the addition, the reaction mixture was stored in the refrigerator (4° C.) overnight. The reaction mixture was washed exhaustively with water (10×300 mL), dried $MgSO_4$, filtered, and concentrated to a yellow oil (53 g crude). The oil was filtered through SiO$_2$ (70–230 mesh) using hexane as eluant. The product was obtained as a clear liquid, 40.25 g, 2,6-Diisopropylallyl benzene A mixture of 2,6-diisopropylphenyl triflate (22.7 g), allyltributyl tin (25.0 g), lithium chloride (9.2 g), and DMF (200 mL) was stirred at room temperature, and the flask was flushed with nitrogen. Bis triphenylphosphine palladium dichloride (0.990 g) was added, and the reaction mixture was heated overnight at 75° C. The reaction mixture was allowed to cool and was then diluted with 300 mL ether. The reaction mixture was washed with water (3×300 mL), dried (MgSO$_4$), filtered, and concentrated to a clear oil. The oil was filtered through SiO$_2$ (70–230 mesh) using hexanes as eluant. Tributyltin chloride was still present, so the oil was taken up in ether (200 mL) and was stirred with water (200 mL) containing potassium fluoride (9.5 g) overnight at room temperature. The mixture was filtered, the layers separated, the organic layer dried over magnesium sulfate, filtered, and concentrated. The residual liquid was filtered 2 times through silica gel using hexanes, then petroleum ether as eluant. The product was obtained as a clear liquid (12.94 g).

2,6-Diisopropylphenylacetic acid

To a mixture of 2,6-diisopropylallyl benzene (10.74 g), carbon tetrachloride (150 mL), acetonitrile (150 mL) was added 34.0 g sodium metaperiodate dissolved in water (400 mL). Then added 0.899 g ruthenium trichloride and vigorously stirred the reaction mixture for 5 hours at room temperature. The reaction was incomplete so added 0.52 g more ruthenium trichloride and stirred overnight at room temperature. The reaction mixture was diluted with methylene chloride (1000 mL). The organic layer was washed with water, dried (MgSO$_4$), filtered, and concentrated to a dark oil. The oil was filtered through silica gel using dichloromethane, then 5% methanol in dichloromethane as eluant. Two products were obtained, 6.25 g of aldehyde as an oil and 1.4 g of acid as a white solid.

2,6-Diisopropylphenylacetyl chloride

A mixture of 2,6-diisopropylphenylacetic acid (0.9 g, 0.004 mol), oxalyl chloride (10 mL), and dimethylformamide (2 drops) was stirred overnight at room temperature. The reaction mixture was concentrated to 0.92 g of a dark oil which was used directly in the next step.

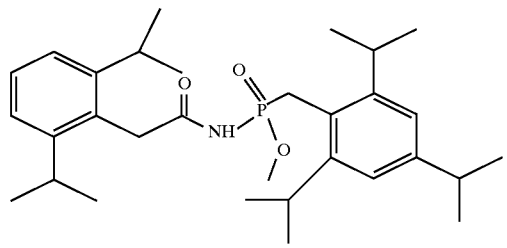

Phosphonamidic acid, N-[[2,6-bis(1-methyl-ethyl)phenyl)acetyl]-P-[[2,4,6-tris(1-methyl-ethyl)phenyl)methyl]-, methyl ester A mixture of 2,6-diisopropylphenylacetyl chloride (0.92 g, 0.0039 mol), monomethyl,2,4,6-triisopropylbenzylphosphonamide (1.22 g, 0.0039 mol), and pyridine (15 mL) was stirred overnight at room temperature and then partitioned between ethyl acetate (200 mL) and water (250 mL). The layers were separated and the organic layer washed with water (3×200 mL), dried (magnesium sulfate), filtered, and concentrated. The residue was chromatographed 2 times on silica gel (70–230 mesh) using 1:1 hexanes/ethyl acetate, then 4:1 hexanes/ethyl acetate as eluant. The product was treated with carbon black in boiling ethyl acetate, filtered through celite, and then passed through florisil using hexanes, then 4:1 hexanes/ethyl acetate as eluant yielding 0.303 g (15%) of product. Analysis calculated for (C$_{31}$H$_{48}$NO$_3$P).

2,4,6-Triisopropylphenylacetyl chloride

A mixture of 2,4,6-triisopropylphenylacetic acid (6.03 g, 0.023 mol), oxalyl chloride (20 mL), and dimethylformamide (3 drops) was stirred vigorously at room temperature and then allowed to stand overnight at room temperature. The reaction mixture was then concentrated to give the product as an off-white solid 6.5 g, 100%. This was used directly in the next step.

Example

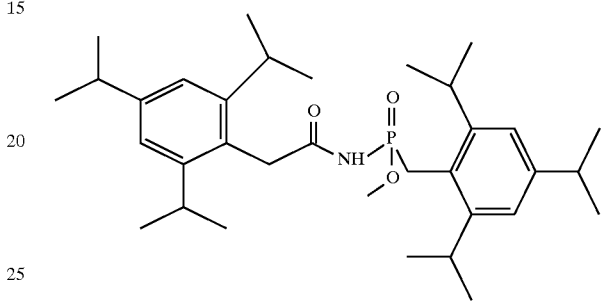

Phosphonamidic acid, N-[[2,4,6-tris(1-methylethyl)phenyl]acetyl]-P-[[2,4,6-tris(1-methylethyl)phenyl]methyl]-, methyl ester A mixture of 2,4,6-triisopropylphenylacetyl chloride (0.281 g, 0.001 mol), monomethyl, 2,4,6-triisopropylbenzylphosphonamide (0.311 g, 0.001 mol), and pyridine (3 mL) was stirred 3 days at room temperature. The reaction mixture was then partitioned between ethyl acetate (150 mL) and water (100 mL), the organic layer was washed with water, dried (magnesium sulfate), filtered, and concentrated. The residue was chromatographed on silica gel (70–230 mesh) using 4:1 hexanes/ethyl acetate as eluant. The product was obtained as an oil which crystallized, 0.3762 g, 67.8%. Analysis calculated for (C$_{34}$H$_{55}$NO$_3$P).

2,6-Diisopropylbenzoic acid 2,6-Diisopropylbromobenzene (21.58 g, 0.0895 mol) was cooled to −23° C. under nitrogen and 2.5M n-butyl lithium in hexanes (36 mL) was added dropwise as the temperature further cooled to −29° C. When the addition was complete, the reaction mixture was warmed to 0° C. and was stirred 1 hour at zero and was then poured onto a large excess of crushed dry ice. The mixture was stirred with a glass rod. When the dry ice had sublimed, hydrochloric acid (1N, 200 mL) was added and the mixture was extracted with ethyl ether, the ether washed with brine, dried (magnesium sulfate), filtered, and concentrated to a yellow oil. The oil was taken up in ether (200 mL), the ether solution extracted with sodium hydroxide solution (1N, 200 mL), the layers separated, the aqueous layer made acidic with 1.5N hydrochloric acid, brine added, and the aqueous layer extracted with ether (200 mL). The ether layer was washed with brine (50 mL), dried (magnesium sulfate), filtered and concentrated to an oil which solidified on standing, 13.42 g, 72.7%.

2,6-Diisopropylbenzoyl chloride

A mixture of 2,6-diisopropylbenzoic acid (12.8 g, 0.062 mol), oxalyl chloride (25 mL), and dimethylformamide (2 drops) was stirred overnight at room temperature. The volatiles were removed on the rotary evaporator and the residue dried to yield an orange oil, 12.65 g, 90.9%.

2,6-Diisopropylbenzyl alcohol

A solution of 2,6-diisopropylbenzoyl chloride (11.65 g, 0.052 mol), in ethyl ether (100 mL) was added over 20 minutes to a suspension of lithium aluminum hydride (1.9 g, 0.050 mol) in ethyl ether (200 mL) keeping the temperature below −15° C. The reaction mixture was allowed to slowly warm to room temperature and was then cooled to zero. The reaction was quenched by careful addition of sodium bisulfate solution until no further reaction was evident. The mixture was diluted with ether (200 mL), the ether washed with brine. The grey goo (lithium/aluminum salts) was washed several times with ether, the ether washes were combined, dried (magnesium sulfate), filtered, and concentrated to an oil which solidified, 10.67 g.

2,6-Diisopropylbenzyl bromide

A solution of phosphorus tribromide (2.5 mL, 0.014 mol) in ethyl ether (20 mL) was added dropwise to 2,6-diisopropylbenzyl alcohol (10.04 g, 0.052 mol) in ethyl ether (250 mL) at room temperature and was stirred overnight at room temperature. Ethanol (95%, 40 mL) was added dropwise over 1 hour and the mixture was stirred 2 hours at room temperature and was then concentrated. The residue was partitioned between ethyl acetate (200 mL) and aqueous sodium bicarbonate. The layers were separated and the organic layer was washed with brine, dried (magnesium sulfate), filtered, and concentrated to an oil, 11.04 g, 83%.

Dimethyl, 2,6-diisopropylbenzyl phosphonate

A mixture of 2,6-diisopropylbenzyl bromide (11.04 g, 0.043 mol) and trimethylphosphite (50 mL) was heated to gentle reflux under nitrogen for 4 hours. The temperature gradually rose to 125° C. Stirred overnight at room temperature, then resumed heating. The temperature gradually rose to 150° C., at which time the reaction mixture was allowed to slowly cool to room temperature. The reaction mixture was then poured into water (400 mL) and was stirred 4 hours at room temperature. The aqueous mixture was extracted with ethyl acetate, the organic layer washed with brine, dried (magnesium sulfate), filtered, and concentrated to an oil. The oil was chromatographed 2 times on silica gel (70–230 mesh) using 1:1 hexanes/ethyl acetate as eluant, yielding 5.66 g (46%) of product. Analysis calculated for ($C_{15}H_{25}O_3P$).

Monomethyl, 2,6-diisopropylbenzyl phosphonate

Dimethyl, 2,6-diisopropylbenzyl phosphonate (5.53 g, 0.019 mol) was dissolved in methanol (25 mL) and 1N sodium hydroxide solution was added followed by enough water till the solution was just cloudy. Just enough methanol was added to make the solution clear. The reaction mixture was boiled on the steambath for about 4 hours and was then allowed to stand overnight at room temperature. Additional 1N sodium hydroxide solution (23 mL) was added and heating was continued for 8 hours. The reaction mixture was allowed to stand at room temperature for 3 days and was then concentrated to remove methanol, water was added, and the solution was washed with ethyl acetate. The aqueous solution was made acidic with 10% citric acid solution, extracted into ethyl acetate (250 mL), washed with brine, dried (magnesium sulfate), filtered, and concentrated to a viscous oil, 4.34 g (82.5%).

Monomethyl, 2,6-diisopropylbenzylphosphonic chloride

Oxalyl chloride (15 mL) was added to monomethyl, 2,6-diisopropylbenzyl phosphonate (4.04 g, 0.015 mol) at room temperature followed by 2 drops of dimethyl formamide. The reaction mixture was stirred overnight at room temperature and then concentrated to an orange oil that solidified on standing, 4.19 g (97%). This was used directly in the next step.

Monomethyl, 2,6-diisopropylbenzylphosphonamide

Monomethyl, 2,6-diisopropylbenzylphosphonic chloride (4.09 g, 0.014 mol) was taken up in ethyl ether (100 mL), added aqueous ammonemia (100 mL), and stirred vigorously at room temperature. Allowed the reaction mixture to stand overnight at room temperature, diluted with ethyl acetate (250 mL), added brine, separated the layers, dried the organic layer over magnesium sulfate, filtered, and concentrated to a white solid. Added hexanes to the solid and collected by filtration, 2.76 g (72%). Anal calculated for ($C_{14}H_{24}NO_2P$): C, 62.44. Found: C, 61.69.

Example 1

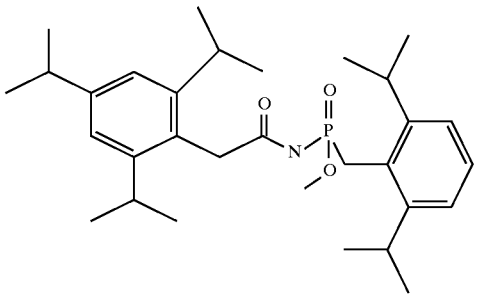

Phosphonamidic acid, P-[[2,6-bis(1-methylethyl)phenyl]methyl]-N-[[2,4,6-tris(1-methylethyl)phenyl]acetyl]-, methyl ester 2,4,6-Triisopropylphenylacetyl chloride (0.789 g, 0.0028 mol) was added to a mixture of monomethyl,2,6-diisopropylbenzylphosphonamide (0.754 g, 0.0028 mol) in pyridine (6 mL) at room temperature. The mixture was stirred 3 days at room temperature and then partitioned between water (500 mL) and ethyl acetate (250 mL). The layers were separated and the organic layer washed with brine (100 mL), dried (magnesium sulfate), filtered, and concentrated to a yellow oil. The oil was chromatographed on silica gel (70–230 mesh) using 4:1 hexanes/ethyl acetate as eluant. The product was obtained as a yellow oil, which yielded a white solid upon trituration with hexanes. The product was obtained in 2 portions, 0.844 g, (58.7%). Analysis calculated for ($C_{31}H_{48}NO_3P$).

[[2,6-bis(1-methyly)phenyl]methyl]phosphoramidate 2,6-Diisopropylphenylmethyl phosphoramidate Sodium hydride (60% in oil, 2.1 g, 0.053 mol) was added over 15 minutes to 2,6-diisopropylphenol (8.9 g, 0.050 mol) in tetrahydrofuran (250 mL) at room temperature. When the reaction had ceased, the phenolate solution was added dropwise to dichloromethylphosphate (6.1 mL, 0.061 mol) in tetrahydrofuran (250 mL) at room temperature. The reaction mixture was stirred 15 minutes at room temperature and then poured into a rapidly stirred mixture of aqueous ammonia (100 mL) and tetrahydrofuran. The entire mixture was stirred 1 hour at room temperature, the layers were separated, the organic layer washed with brine (2×100 mL), dried (magnesium sulfate), filtered, and concentrated to an oil which solidified. The solid was filtered through silica gel (70–230 mesh) using 1:1 hexanes/ethyl acetate as eluant. The product was obtained as a white solid, 1.74 g (12.9%). Analysis calculated for ($C_{13}H_{22}NO_3P$).

Phosphoramidic acid, [[[2,6-bis(1-methyl-ethyl)phenyl]-amino]carbonyl]-, methyl 2,6-bis(1-methylethyl) phenyl ester 2,6-Diisopropylphenylmethyl phosphoramidate (0.534 g, 0.002 mol) was taken up in tetrahydrofuran (20 mL), 2,6-diisopropylphenyl isocyanate (0.44 g, 0.0022 mol) was added, followed by sodium hydride (60% in oil, 0.085 g, 0.0021 mol), and the mixture was stirred overnight at room temperature. The reaction mixture was concentrated to dryness, partitioned between ethyl acetate (200 mL) and aqueous citric acid solution (10%, 50 mL), the layers were separated, the organic layer washed with brine (50 mL), dried (magnesium sulfate), filtered, and concentrated to a white solid. The solid was filtered 2 times through silica gel (70–230 mesh) using 4:1 hexanes/ethyl acetate as eluant. The product-containing fractions were concentrated to a white solid, 0.715 g, (75%). Analysis calculated for ($C_{26}H_{39}N_2O_4P$): C, 65.80. Found: C, 67.019.

Example 2

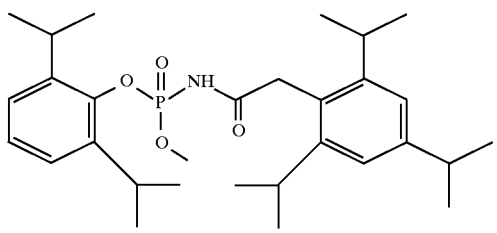

[(2,4,6-Triisopropyl-phenyl)-acetyl]-phosphoramidic acid 2,6-diisopropyl-phenyl ester methyl ester 2,6-Diisopropylphenylmethyl phosphoramidate (0.53 g, 0.002 mol) and 2,4,6-triisopropylphenylacetyl chloride (0.57 g, 0.002 mol) were mixed in tetrahydrofuran (10 mL) and sodium hydride (60% in oil, 0.095 g, 0.024 mol) was added, and the reaction mixture was allowed to stand at room temperature for 1.5 hours. The reaction mixture was concentrated to a yellow oil, partitioned between ethyl acetate (100 mL) and 10% aqueous citric acid solution (50 mL), the layers separated, the organic layer washed with brine, dried (magnesium sulfate), filtered, and concentrated to an oil. The oil was chromatographed on silica gel (70–230 mesh) using 4:1 then 1:1 hexanes/ethyl acetate as eluant. The product was obtained as a white solid from hexanes, 0.137 g, (13.3%). Analysis calculated for ($C_{30}H_{46}NO_4P$).

4-Chloro-2,6-diisopropylphenylmethyl phosphoramidate

This compound was prepared as for 2,6-diisopropylphenylmethyl phosphoramidate except that 4-chloro-2,6-diisopropylphenol was substituted for 2,6-diisopropylphenol.

Example 3

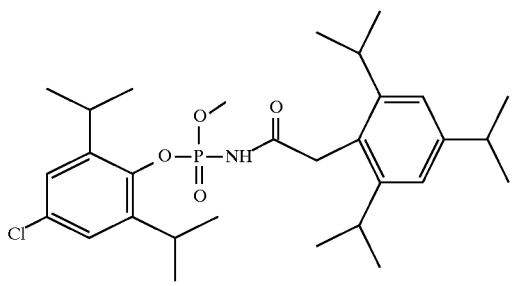

Phosphoramidic acid, [[2,4,6-tris(1-methylethyl)phenyl]acetyl]-, 4-chloro-2,6-bis(1-methylethyl)phenyl methyl ester
[(2,4,6-Triisopropyl-phenyl)-acetyl]-phosphoramidic acid 4-Chloro-2,6-diisopropyl-phenyl ester methyl ester A mixture of 4-chloro-2,6-diisopropylphenylmethyl phosphoramidate (0.603, 0.002 mol) and 2,4,6-triisopropylphenylacetyl chloride (0.580 g, 0.0021 mol) were heated neat on the steambath for 3 hours. The reaction mixture was chromatographed on silica gel (70–230 mesh) using 4:1 then 1:1 hexanes/ethyl acetate as eluant. The product was obtained as a solid upon trituration with hexanes, 0.135 g, (12.3%). Analysis calculated for ($C_{30}H_{45}ClNO_4P$).

Phenylphosphonamide, 2,6-bis(1-methylethyl)phenyl ester
Phenylphosphonamide, 2,6-diisopropylphenyl ester This compound was prepared as 2,6-diisopropylphenyl ethyl phosphoramidate except that phenylphosphonic dichloride was substituted for dichloromethylphosphate. Analysis calculated for ($C_{18}H_{24}NO_2P$).

Example 4

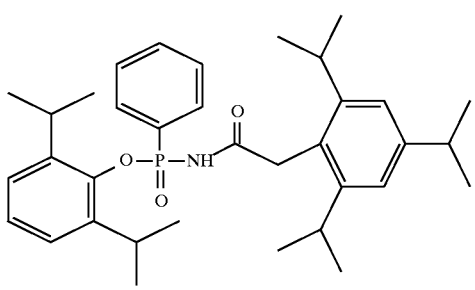

This compound was prepared according to the procedure for phosphonamidic acid, N-[[2,4,6-tris(1-methylethyl)phenyl]acetyl]-P-[[2,4,6-tris(1-methylethyl)phenyl]methyl]-, methyl ester except that the 2,6-diisopropylphenyl ester of benzene-phosphonamide was substituted for 2,4,6-triisopropylbenzylphosphonamide monomethyl ester. Analysis calculated for ($C_{35}H_{48}NO_3P$).

N-(2,4,6-Triisopropylbenzyl)phthalimide

A mixture of 2,4,6-triisopropylbenzyl bromide (5.00 g, 16.8 mmol), potassium phthalimide (3.71 g, 19.9 mmol), and dimethylformamide were heated for 3 hours at 70° C. The reaction mixture was allowed to stand overnight at room temperature and was then heated at 90° C. for 1 hour. The solvent was removed on the rotary evaporator, ethyl acetate (250 mL) was added, the organic layer was washed with brine, dried over magnesium sulfate, filtered, and concentrated to a white solid. Hexanes (50 mL) and ethyl acetate (5 mL) was added and the solid collected by filtration, 4.18 g (68%). An analytical sample was obtained by silica gel filtration using 9:1, hexanes/ethyl acetate as eluant. Analysis calculated for ($C_{24}H_{29}NO_2$).

2,4,6-Triisopropylbenzylamine

A mixture of N-(2,4,6-triisopropylbenzyl)phthalimide (4.62 g, 13.7 mmol), hydrazine hydrate (0.5 mL), and methanol (150 mL) was heated on the steambath for 3 hours, at which time 0.3 mL more hydrazine hydrate was added. The reaction mixture was allowed to stand overnight at room temperature. Methanol (150 mL) was added and heated on the steambath. The methanol was removed on the rotary evaporator without heating. The reaction mixture was diluted with water (300 mL) and extracted with dichloromethane (1×200 mL and 1×100 mL), the extracts were combined, dried (magnesium sulfate), filtered, and concentrated. The residue was filtered through silica using ethyl acetate as eluant. The product was obtained as an oil, 1.93 g, (65%).

2,4,6-Triisopropylbenzylphosphonate dibenzyl ester

Sodium hydride (2.0 g, 50 mmol), was added in portions to dibenzylphosphite (13.0 g, 50 mmol) in tetrahydrofuran (250 mL) at room temperature. When no further reaction was apparent, added 2,4,6-triisopropylbenzyl bromide (14.47 g, 49 mmol) and stirred at room temperature. Stirred overnight at room temperature, added more phosphite anion (11.94 g phosphite, 1.30 g NaH), and stirred over 2 days at room temperature. The reaction mixture was concentrated, the residue was taken up in ethyl acetate, washed with 10% aqueous citric acid solution, brine, dried (magnesium sulfate), filtered, and concentrated to an oil. The oil was chromatographed on silica gel using 4:1 hexanes/ethyl acetate as eluant. The product was obtained as a solid in two portions, 17.47 g, (73%). Analysis calculated for ($C_{30}H_{39}O_3P$).

2,4,6-Triisopropylbenzylphosphonate monobenzyl ester 2,4,6-Triisopropylbenzylphosphonate dibenzyl ester (9.56 g, 20 mmol) in methanol (120 mL) was treated with 1N sodium hydroxide solution, and the mixture was boiled until no methanol remained. Added methanol (150 mL) and again boiled until only the aqueous layer remained. Added 25 mL more 1N sodium hydroxide solution and ethanol (150 mL). The mixture was boiled on the steambath and was then allowed to stand overnight at room temperature. Added 50% sodium hydroxide (2 mL) and concentrated to remove ethanol. Washed the organic layer with ethyl acetate, made the aqueous layer acidic with 10% citric acid solution, added brine, and extracted with ethyl acetate. The layers were separated, the organic layer was washed with brine, dried (magnesium sulfate), filtered, and concentrated to a tan oil/solid. Added hexanes, filtered the solution through cotton, and allowed the solution to stand at room temperature. The resulting solid was collected by filtration. The product was obtained in 2 portions, 1.71 g, (22%). Analysis calculated for ($C_{23}H_{33}O_3P \cdot H_2O$).

Monobenzyl, 2,4,6-triisopropylbenzylphosphonic chloride

Excess oxalyl chloride (10 mL) was added to 2,4,6-triisopropylbenzylphosphonate monobenzyl ester (1.58 g, 4.1 mmol) at room temperature. One drop of dimethylformamide was added to the reaction, and the mixture was stirred overnight at room temperature and then concentrated in vacuo to yield 1.67 g of a viscous yellow oil which was used directly in the next step.

Monobenzyl, 2,4,6-triisopropylbenzylphosphonamide

A mixture of diethyl ether (100 mL) and saturated aqueous ammonia (100 mL) was added to a rapidly stirred solution of monobenzyl,2,4,6-triisopropylbenzylphosphonic chloride (1.67 g, 4.1 mmol) at room temperature. The reaction mixture was stirred 1.5 hours at room temperature. The volatiles were removed on the rotary evaporator, ethyl acetate was added, the layers were separated, the organic layer was washed with brine, dried (magnesium sulfate), filtered, and concentrated to an oil which crystallized. Hexanes was added to the solid which was collected by filtration yielding 0.96 g, (60%). Analysis calculated for ($C_{23}H_{34}NO_2P$).

Monobenzyl, (N-2,4,6-triisopropylphenylacetyl)-2,4,6-triisopropylbenzylphosphonamide Pyridine (5 mL) was added to a mixture of monobenzyl-2,4,6-triisopropylbenzylphosphonamide (0.765 g, 2.0 mmol) and 2,4,6-triisopropylphenylacetyl chloride (0.605 g, 2.2 mmol), and the mixture was stirred 4 days at room temperature. The reaction mixture was diluted with ethyl acetate (150 mL) and was washed with 10% aqueous citric acid solution (1×100 mL), water (2×100 mL), and brine (1×50 mL), dried (magnesium sulfate), filtered, and concentrated to a yellow oil. The oil was filtered through silica gel using 4:1 hexanes/ethyl acetate as eluant. The product-containing fractions were chromatographed on silica gel using 9:1 hexanes/ethyl acetate as eluant. The product, 0.20 g (17%), was obtained as a white foam. Analysis calculated for ($C_{40}H_{58}NO_3P$).

(N-2,4,6-triisopropylbenzyl)-2,4,6-triisopropylbenzylphosphonamide monobenzyl ester A mixture of monobenzyl,2,4,6-triisopropylbenzylphosphonic chloride (0.45 g, 1.1 mmol), 2,4,6-triisopropylbenzylamine (0.256 g, 1.1 mmol), triethylamine (1 mL), and ethyl acetate (6 mL) was allowed to stand 3 days at room temperature. The reaction mixture was diluted to 100 mL with ethyl acetate, washed with 10% aqueous citric acid solution (100 mL), brine (50 mL), dried (magnesium sulfate), filtered, and concentrated to a yellow oil. The oil was chromatographed on silica gel using 4:1, hexanes/ethyl acetate as eluant yielding 0.346 g (52%) of a yellow oil.

We claim:

1. Compounds of the formula (I)

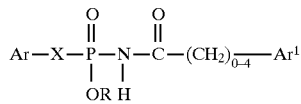

or a pharmaceutically acceptable salt thereof wherein:

Ar and $Ar^1$ are each independently selected from substituted phenyls which substituents are from 1–5 in number and at least one is at the ortho position and are each independently selected from alkyl, alkoxy, hydroxy, halogen, nitro, trifluoromethyl, COOH, and COOalkyl, X is —($CH_2$)$_{0-4}$—; and R is hydrogen, alkyl, or phenyl.

2. A compound according to claim 1 wherein

Ar is phenyl with at least 1 ortho substituent;

$Ar^1$ is phenyl with at least 1 ortho substituent;

X is —($CH_2$)$_{0-4}$—; and

R is hydrogen, alkyl, phenyl.

3. A compound of formula I

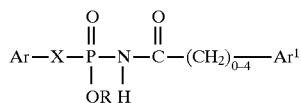

or a pharmaceutically acceptable salt thereof wherein Ar is phenyl substituted with 3 substituents each independently selected from isopropyl and chloride;

$Ar^1$ is phenyl substituted with 3 isopropyl substituents; and

X is $CH_2$.

4. A pharmaceutical composition for regulating plasma cholesterol concentration comprising an effective amount of a compound of formula I

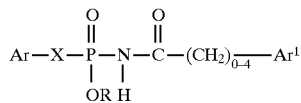

or a pharmaceutically acceptable salt thereof wherein:

Ar and $Ar^1$ are each independently selected from substituted phenyls which substituents are from 1–5 in number and are each independently selected from alkyl, alkoxy, hydroxy, halogen, nitro, trifluoromethyl, COOH, and COOalkyl;

X is —($CH_2$)$_{0-4}$—; and

R is hydrogen, alkyl, or phenyl, and a pharmaceutically acceptable carrier.

5. A method of treating hypercholesterolemia comprising administering to a patient a therapeutically effective amount of a compound of formula I

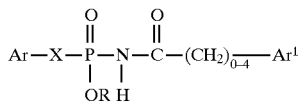

or a pharmaceutically acceptable salt thereof wherein:

Ar and $Ar^1$ are each independently selected from substituted phenyls which substituents are from 1–5 in number and are each independently selected from alkyl, alkoxy, hydroxy, halogen, nitro, trifluoromethyl, COOH, and COOalkyl;

X is $-(CH_2)_{0-4}-$; and

R is hydrogen, alkyl, or phenyl.

6. A method of treating atherosclerosis comprising administering to a patient a therapeutically effective amount of a compound of formula I

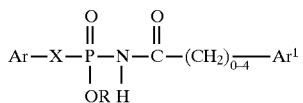

or a pharmaceutically acceptable salt thereof wherein:

Ar and $Ar^1$ are each independently selected from substituted phenyls which substituents are from 1–5 in number and are each independently selected from alkyl, alkoxy hydroxy, halogen, nitro, trifluoromethyl, COOH, and COOalkyl;

X is $-(CH_2)_{0-4}-$; and

R is hydrogen, alkyl, or phenyl.

7. A compound according to claim 1 selected from:

Phosphonamidic acid, N-[[2,6-bis(1-methylethyl)phenyl)acetyl]-P-[[2,4,6-tris(1-methylethyl)phenyl)methyl]-, methyl ester;

Phosphonamidic acid, P-phenyl-N-[[2,4,6-tris(1-methylethyl)phenyl]acetyl]-, 2,6-bis(1-methylethyl)phenyl ester;

Phosphonamidic acid, P-[[2,6-bis(-1methylethyl)phenyl]methyl]-N-[[2,4,6-tris(1-methylethyl)phenyl]acetyl]-, methyl ester; and Phosphonamidic acid, N-[[2,4,6-tris(1-methylethyl)phenyl]acetyl]-P-[[2,4,6-tris(1-methylethyl)phenyl]methyl]-, methyl, ester.

* * * * *